(12) United States Patent
McLoughlin et al.

(10) Patent No.: US 12,102,595 B2
(45) Date of Patent: Oct. 1, 2024

(54) SERIALLY-CONNECTABLE DRUG MODULES FOR COMBINATORIAL DRUG DELIVERY DEVICE

(71) Applicant: Bristol-Myers Squibb Company, Princeton, NJ (US)

(72) Inventors: Martin John McLoughlin, Hillsborough, NJ (US); Mark Steven Howansky, Green Brook, NJ (US); Stephen Lawrence Zieminski, Brunswick, NJ (US); Chester Larrow, Baltimore, MD (US); Mariano Mumpower, Baltimore, MD (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 844 days.

(21) Appl. No.: 17/047,262

(22) PCT Filed: May 10, 2019

(86) PCT No.: PCT/US2019/031762
§ 371 (c)(1),
(2) Date: Oct. 13, 2020

(87) PCT Pub. No.: WO2019/217845
PCT Pub. Date: Nov. 14, 2019

(65) Prior Publication Data
US 2021/0154097 A1 May 27, 2021

Related U.S. Application Data

(60) Provisional application No. 62/670,266, filed on May 11, 2018.

(51) Int. Cl.
*A61J 1/20* (2006.01)
*A61J 1/14* (2023.01)
(Continued)

(52) U.S. Cl.
CPC ............... *A61J 1/20* (2013.01); *A61J 1/1475* (2013.01); *A61J 1/16* (2013.01); *A61J 1/2006* (2015.05);
(Continued)

(58) Field of Classification Search
CPC .. A61J 1/065; A61J 1/1475; A61J 1/16; A61J 1/20; A61J 1/2006; A61J 1/2089;
(Continued)

(56) References Cited

U.S. PATENT DOCUMENTS

2002/0004643 A1  1/2002 Carmel et al.
2009/0062732 A1  3/2009 Radmer
(Continued)

FOREIGN PATENT DOCUMENTS

CN  1668352 A  9/2005
CN  101442972 A  5/2009
(Continued)

OTHER PUBLICATIONS

International Search Report and Written Opinion of the International Searching Authority from PCT International Application No. PCT/US2019/031762, dated Jul. 17, 2019.
(Continued)

*Primary Examiner* — John Kim
(74) *Attorney, Agent, or Firm* — Budzyn IP Law, LLC

(57) ABSTRACT

A combinatorial drug delivery device is provided for delivering a predetermined selection of drug components, each of the drug components being contained in a drug vial. The device includes a plurality of modules, wherein each of the modules includes: a body having an interior volume formed to accommodate a drug vial; a cannula protruding into the interior volume, the cannula terminating at a free end, first and second openings being formed in the free end with first and second lumens extending therefrom and through the
(Continued)

cannula; a socket located on an exterior portion of the body; a first passageway extending between, and in communication with, the socket and the first lumen; a boss protruding from an exterior portion of the body; and, a second passageway extending from, and in communication with the second lumen, the second passageway extending through the boss to terminate at an exit opening formed therein.

12 Claims, 14 Drawing Sheets

(51) Int. Cl.
    *A61J 1/16*         (2023.01)
    *A61J 3/00*         (2006.01)
    *A61M 5/14*        (2006.01)
    *A61M 5/142*       (2006.01)

(52) U.S. Cl.
    CPC ............ *A61J 1/201* (2015.05); *A61J 1/2058* (2015.05); *A61J 1/2068* (2015.05); *A61J 1/2075* (2015.05); *A61J 1/2089* (2013.01); *A61J 3/002* (2013.01); *A61M 5/1407* (2013.01); *A61M 5/1408* (2013.01); *A61M 5/1409* (2013.01); *A61M 5/1413* (2013.01); *A61M 5/14248* (2013.01); *A61M 2005/14268* (2013.01); *A61M 2209/045* (2013.01)

(58) Field of Classification Search
    CPC ........ A61J 1/201; A61J 1/2058; A61J 1/2075; A61J 1/2068; A61J 3/002; A61M 5/1407; A61M 5/1408; A61M 5/1409; A61M 5/1413; A61M 5/14248; A61M 2209/045; A61M 2005/14268
    See application file for complete search history.

(56) References Cited

U.S. PATENT DOCUMENTS

| | | |
|---|---|---|
| 2013/0253430 A1 | 9/2013 | Kouyoumjian et al. |
| 2015/0257974 A1 | 9/2015 | Demers et al. |
| 2017/0020784 A1* | 1/2017 | Schweiss .............. A61J 1/2089 |

FOREIGN PATENT DOCUMENTS

| | | |
|---|---|---|
| CN | 105339024 A | 2/2016 |
| WO | 2007107406 A2 | 9/2007 |
| WO | 2012092564 A2 | 7/2012 |
| WO | 2016205687 A1 | 12/2016 |

OTHER PUBLICATIONS

Search Report from Chinese Patent Application No. 2019800313543 dated Dec. 15, 2023.

* cited by examiner

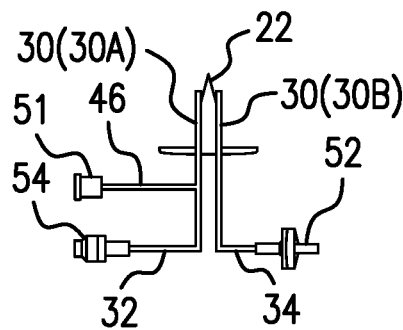
FIG.6
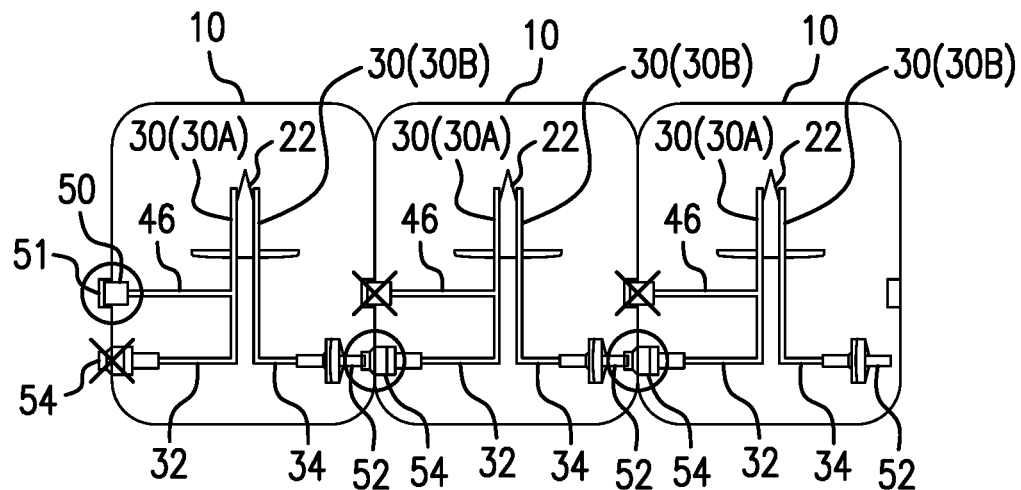
FIG.7
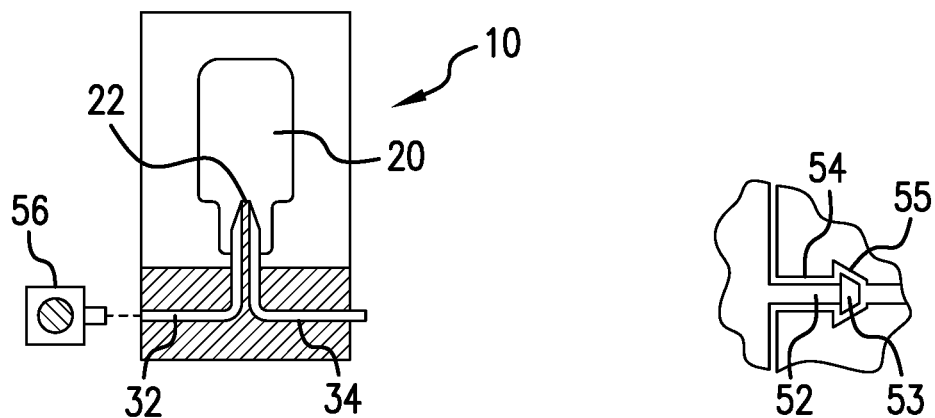
FIG.8
FIG.8A

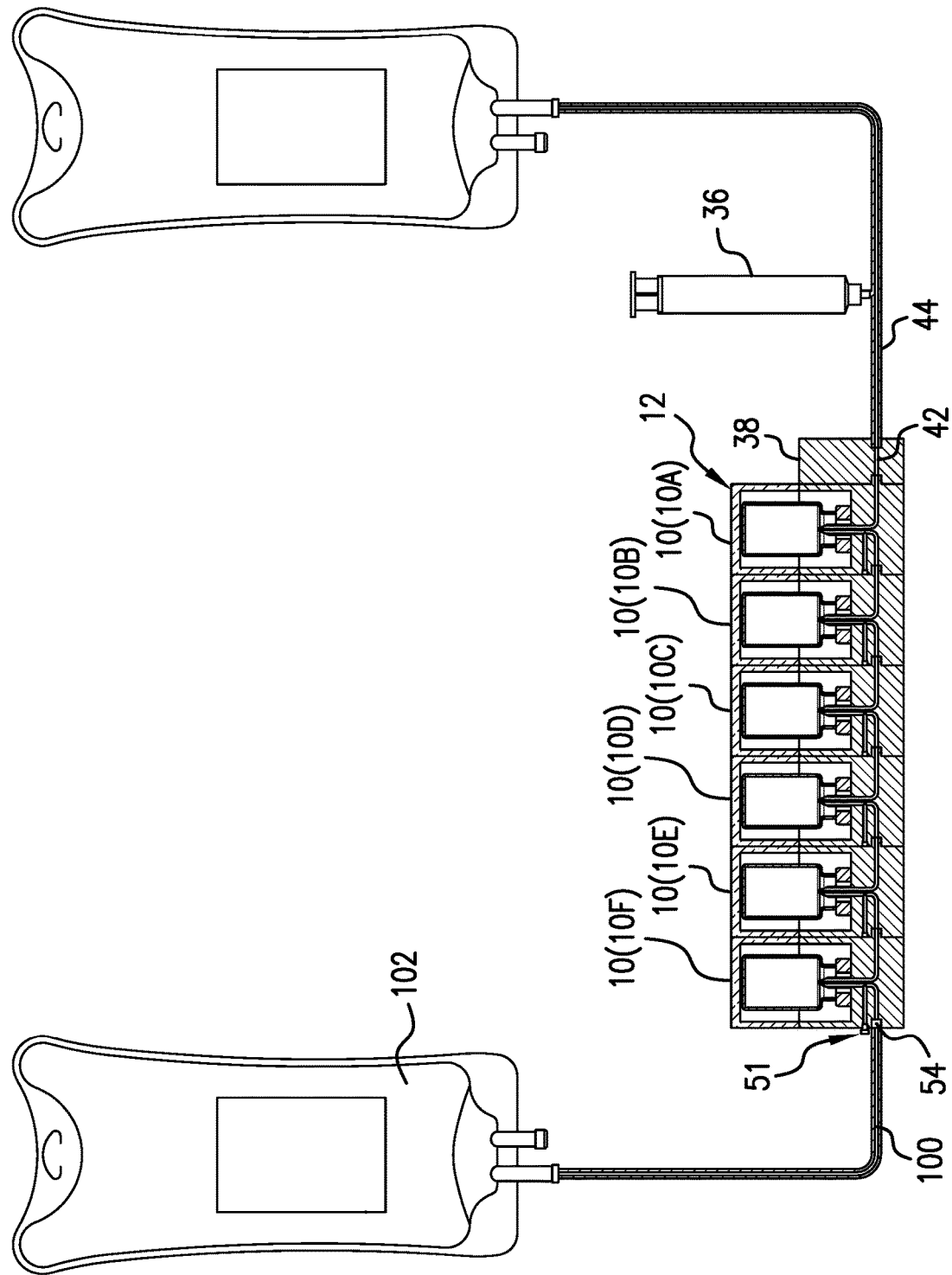

SERIALLY-CONNECTABLE DRUG MODULES FOR COMBINATORIAL DRUG DELIVERY DEVICE

FIELD OF THE INVENTION

The field of the present invention is the compounding and preparation of liquid drugs, especially for intra-venous infusion and direct patient administration. More particularly the invention relates to devices for the preparation and compounding of combinations of two or more drugs.

BACKGROUND OF THE INVENTION

It is common practice in the administration of drugs by intravenous infusion for the drugs to be compounded within a pharmacy environment. Such drugs are typically supplied sterile in glass vials and may be supplied in solid or aqueous solution form. When supplied in solid form the drugs must be reconstituted with a sterile aqueous diluent prior to transfer to the infusion bag. The person skilled in the art will appreciate that such drug formulations will typically include several excipients for example buffers, pH modifiers, tonicity modifiers, stabilizers and so on. Typically liquid drugs for intra-venous infusion are compounded in an infusion bag in a pharmacy environment prior to transfer to the patient for infusion. Because of the need to maintain sterility of the drugs while compounding the compounding procedure is typically performed in an aseptic pharmacy hood. Typically the pharmacist or pharmacy technician (practitioner) will prepare the drugs in accordance with an individual patient prescription.

After ensuring the hood is clear of all materials the practitioner will retrieve vials of the drugs required per the prescription from the pharmacy stocks and will verify their identity and strength. The verification process may be assisted by use of a bar code scanner or other identification technology. The practitioner will also pick from stock all of the other necessary equipment required to safely prepare the drugs for infusion including the infusion bag itself, syringes, needles, transfer sets, gloves, sharps disposal containers and so on. Once all of the necessary equipment has been assembled the practitioner will follow a protocol for the preparation of the drugs which may include the reconstitution of solid drugs by addition of diluents, the ordered withdrawal of liquid drugs from their individual vials into the IV bag via the transfer port. Typically this procedure is performed manually and involves the use of multiple needles. The risk of needle-stick injuries to the practitioner is increased by each needle required to effect the compounding of the drugs. With high potency or toxicity drugs, e.g. cytotoxic agents for chemotherapy, this presents a considerable exposure risk for the practitioner.

To eliminate some of the risks associated with manual preparation including exposure to dangerous drugs and the risk of medication errors, pharmacy compounding machines are known to the person skilled in the art which automate many of the steps involved in the preparation and compounding of drugs. Typically such machines are complex electromechanical systems which implement sophisticated precision dispensing mechanisms for the accurate reconstitution of liquid drugs. Aside from their cost, size and complexity, many of the designs for such machines described in the art draw liquid drugs from a stock reservoir and so only use a fraction of the drug in the container. Because of the need to maintain sterility, unused drug solutions must typically be discarded and so are wasted. With the very high cost of some drugs, especially biologic drugs, this waste is a significant undesirable cost. When the wasted drugs are cytotoxic agents, their disposal creates a significant environmental and safety hazard.

Recent advances in medicine, particularly in the treatment of cancer, have demonstrated that therapeutically beneficial effects can be achieved by the synergistic combination of two or more drugs. For example, recent clinical research has demonstrated that the combination of an anti-PD-1 checkpoint inhibitor drug with a CTLA-4 checkpoint inhibitor can have beneficial synergistic effects in some tumor types which can lead to better clinical outcomes than could be achieved by the individual administration of either drug alone. Typically such checkpoint inhibitor drugs are biotechnology derived monoclonal antibodies or fragments thereof of the immunoglobulin type. In some situations it may be beneficial to combine such biologic drugs with conventional chemotherapy agents such as cytotoxic drugs.

Applicant has now realized that the combinatorial principles described in U.S. Provisional Patent Application No. 62/670,266, filed on May 11, 2018, to the same assignee as herein, and which is incorporated herein by reference in its entirety, can address several of the challenges encountered in the preparation and compounding of drugs for intra-venous infusion and can provide several advantages including but not limited to simplification of pharmacy procedures, reduction in the risk of medication errors, containment and protection for the practitioner from highly potent or highly toxic agents, reduction in the risk of needle-stick injuries, reduction or elimination of drug waste, avoidance of the need for complex and expensive pharmacy compounding machines. As a consequence of these advantages in embodiments the present invention may further enable the preparation and compounding of drugs for IV infusion and direct administration to a patient at locations remote from the pharmacy, and by a non-specialist practitioner, for example by a suitably trained technician or nurse at the patient's home. This possibility is enhanced by the intrinsic portability of the system described herein.

SUMMARY OF THE INVENTION

According to the present invention, there are provided drug modules each defining a chamber for the receipt of a drug filled vial. In embodiments, spacing adapters may be provided, or vial-retaining dimensions may be altered, to enable the receipt of different sized vials. The modules may further comprise a displaceable vial retainer to allow access to the vial septum for disinfection, a cannula arranged to breach the vial septum on displacement of the vial retainer, sterile tubing defining a sterile fluid path from the cannula to the inlet and outlet ports which connect the sterile fluid paths on adjacent modules. The modules also may comprise male and female mating features such that any number of modules of identical design can attach to each other in a 'stack'. Further the mating features and ports may be arranged so that the fluidic connections between the modules are made automatically when modules are serially connected together via their respective mating features. Each module may be also provided with a vent, including a vent terminated by an aseptic particulate filter that enables the equalization of pressure within the vial during removal of liquid drug from the vial whilst preventing the entrainment of contaminants into the fluid path. The vents may be arranged such that when another module is mated adjacent to the vent side of the module, a seal is formed which blocks that vent. In this way, only the terminal module on a stack may be vented to atmosphere.

The first module in the stack may be connected to a housing which comprises a male port similar to that provided on the modules. The housing comprises further sterile tubing, which may extend from the housing and be terminated by a sterile hollow needle which may be used to breach the sterile port on an infusion bag or other container for the pumped transfer of liquid drugs into the bag or other container, or may be used for drug administration directly into a patient. Further pumping means may be provided so that when fully connected the liquid drugs in the vials may be pumped as one from their respective vials to the needle.

In embodiments such pumping means may be integral to the housing or may be external to the housing. The pumping means may be sterile and form a component of the fluid path or may be of the non-contacting variety such as peristaltic pumps. The person skilled in the art will be familiar with several pumping technologies suitable for use in the pumped transfer of liquid drugs in the manner described.

BRIEF DESCRIPTION OF THE DRAWINGS

FIGS. 6 and 7 depict fluid and venting passageways usable with the modules of the subject invention;

FIG. 8 depicts a venting module usable with the subject invention;

FIG. 8A shows a locking arrangement usable with the subject invention;

DETAILED DESCRIPTION

With reference to the Figures, modules 10 formed in accordance with the subject invention are shown which are serially connectable to form a combinatorial drug delivery device 12. To minimize the number of components needed in inventory, it is preferred that the modules 10 be similarly formed. The modules 10 may be formed with adjustable features to correspond to any contained drugs.

Figure 16A:
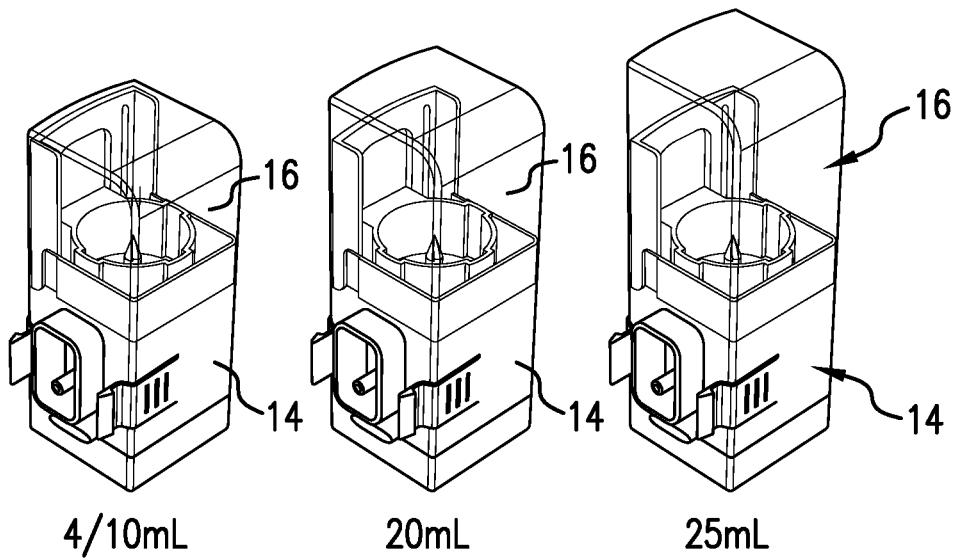
FIGS. 16A-16B depict different modules adapted to accommodate different size drug vials; and, FIG. 17 depicts a drug delivery device coupled to a collapsible reservoir of diluent.
Figure 16B:
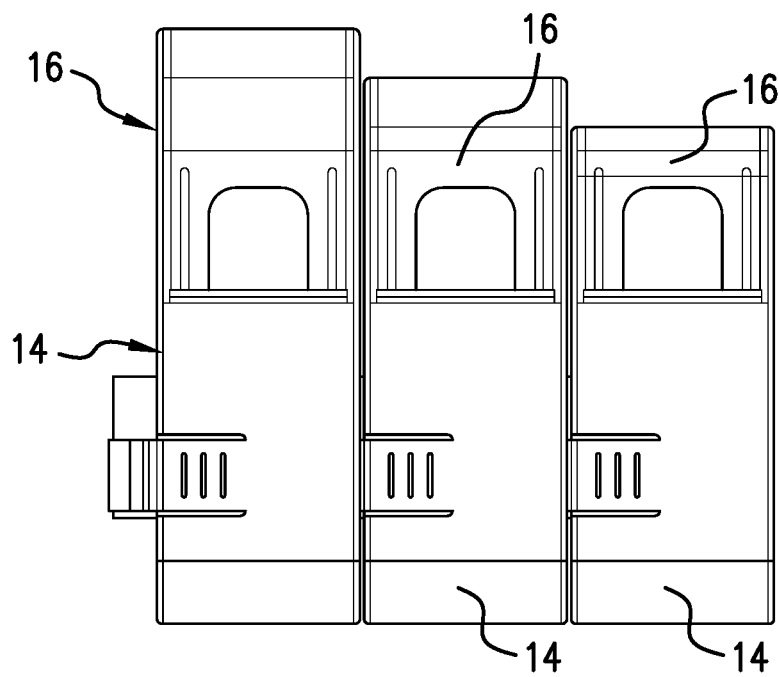

As shown in the Figures, each of the modules 10 is generally box shaped with a body 14 and a vial retainer 16, with the body 14 enclosing an interior volume 18. The vial retainer 16 is displaceable relative to the body 14, including possibly being hingedly attached to the body 14. The vial retainer 16 is shaped and dimensioned to accommodate a drug vial or container 20. To accommodate drug vials 20 of various sizes, adapter(s) or spacer(s) may be provided for placement into the vial retainer 16 to accommodate various sized drug vials 20. Typically, the size (i.e., volume) of the drug vials 20 will be varied by altering the length thereof. With this arrangement, the vial retainer 16 may be configured to accommodate a largest drug vial size without any adapters or spacers, as shown in FIGS. 16A and 16B. In this manner, the modules 10 may be coupled as described below with the modules 10 accommodating drug vials 20 of different volumes.

Figure 1:
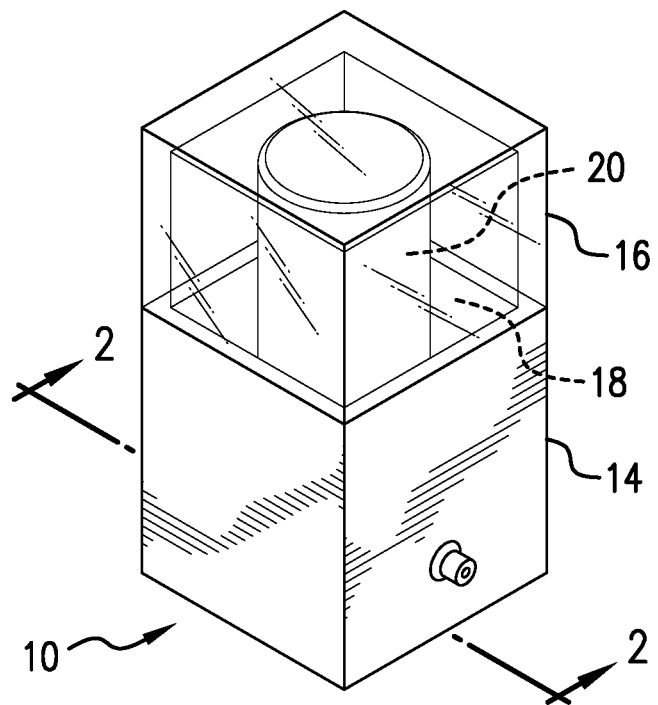
FIG. 1 is a perspective view of a module formed in accordance with the subject invention.
Figure 2:
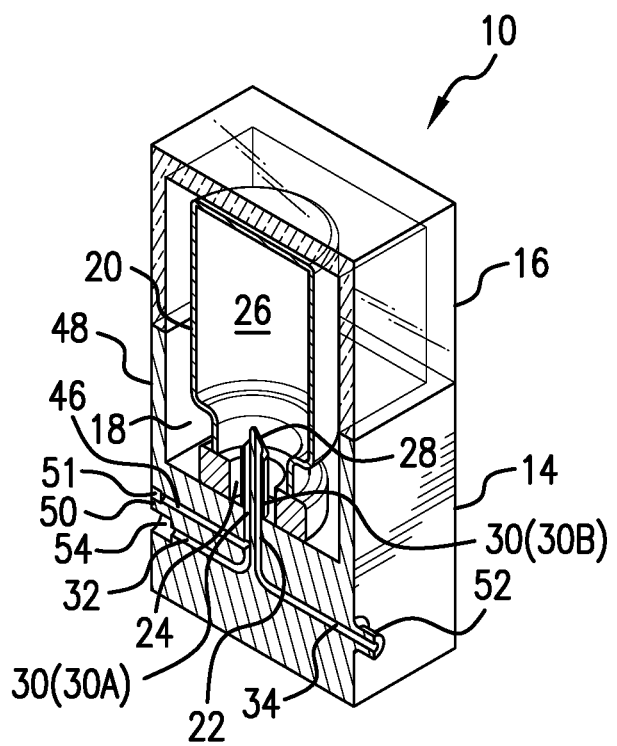
FIG. 2 is a cross-sectional view taken along line 2-2 of FIG. 1.

As shown in FIG. 2, each of the modules 10 includes a cannula 22 extending into the interior volume 18 positioned to pierce a septum 24 of an accommodated drug vial 20 in accessing interior volume 26 of the drug vial 20. A distal end 28 of the cannula 22 may be sharpened to facilitate piercing of the septum 24. The cannula 22 must be provided with sufficient length to fully pierce the septum 24 in accessing the interior volume 26.

The cannula 22 preferably includes multiple inner lumens 30, such as primary inner lumen 30A and secondary inner lumen 30B. With this arrangement, with the cannula 26 piercing the septum 24, all of the inner lumens 30 are in communication with the interior volume 26 of the drug vial 20. The inner lumens 30 extend through the cannula 22 away from the distal end 28 and into the body 14. A primary passageway 32 is provided in communication with the primary inner lumen 30A, and a secondary passageway 34 is provided in communication with the secondary inner lumen 30B. With this arrangement, liquid may flow in and out of the interior volume 26, e.g., with one-way flow travelling from the primary passageway 32, through the primary inner lumen 30A, into the interior volume 26, through the secondary inner lumen 30B, and through the secondary passageway 34. This allows for both introduction of liquid into the drug vial 20 and removal of liquid therefrom. The primary and secondary passageways 32, 34 may be formed by portions of the body 14, e.g., the passageways being etched into the body 14 or formed by other material removal processes. In addition, the primary and secondary passageways 32, 34 may be defined by tubing which passes through channels formed in the body 14.

Figure 3:
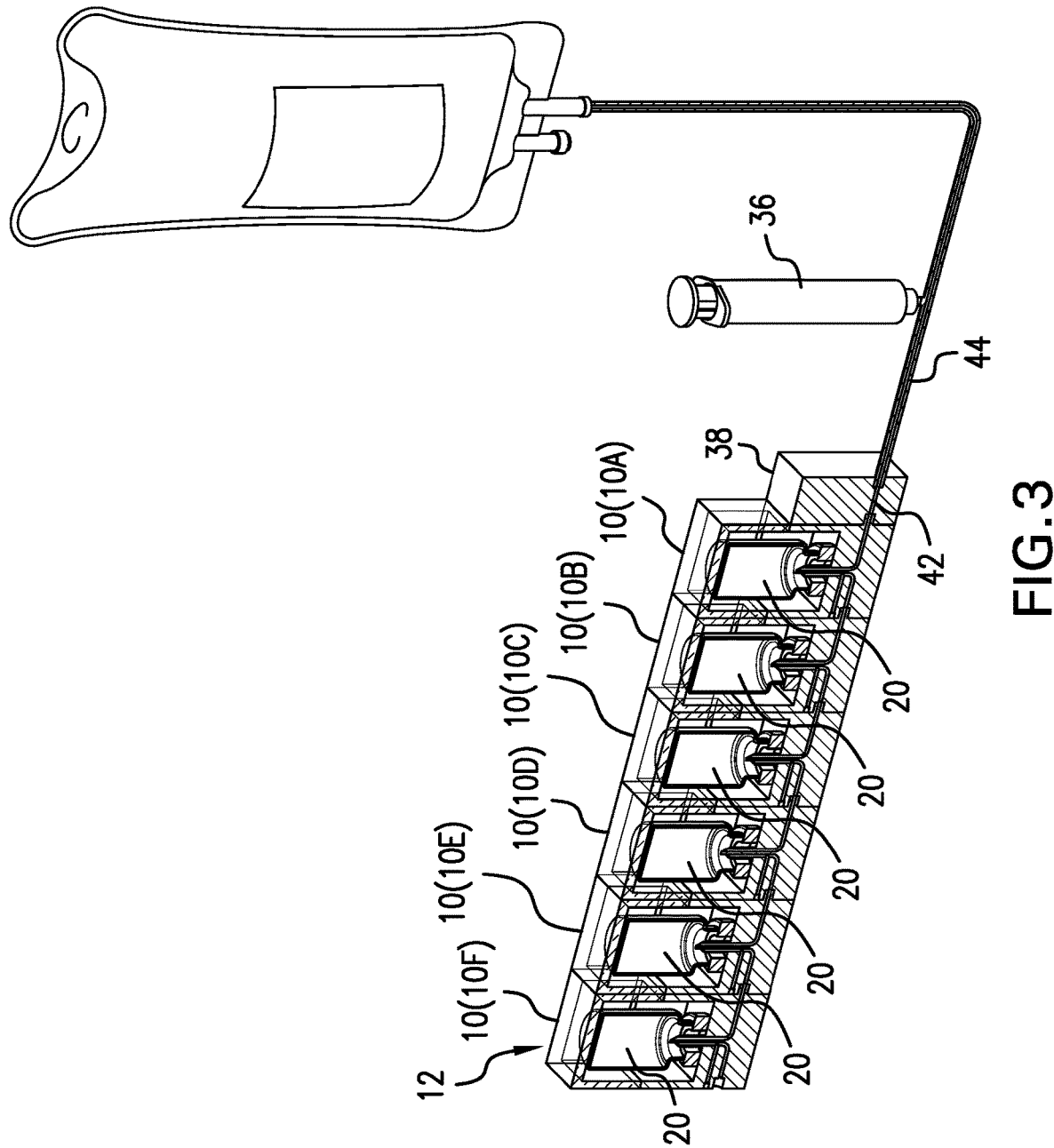
FIGS. 3-5 are cross-sectional views of a drug delivery device in accordance with the subject invention.
Figure 4:
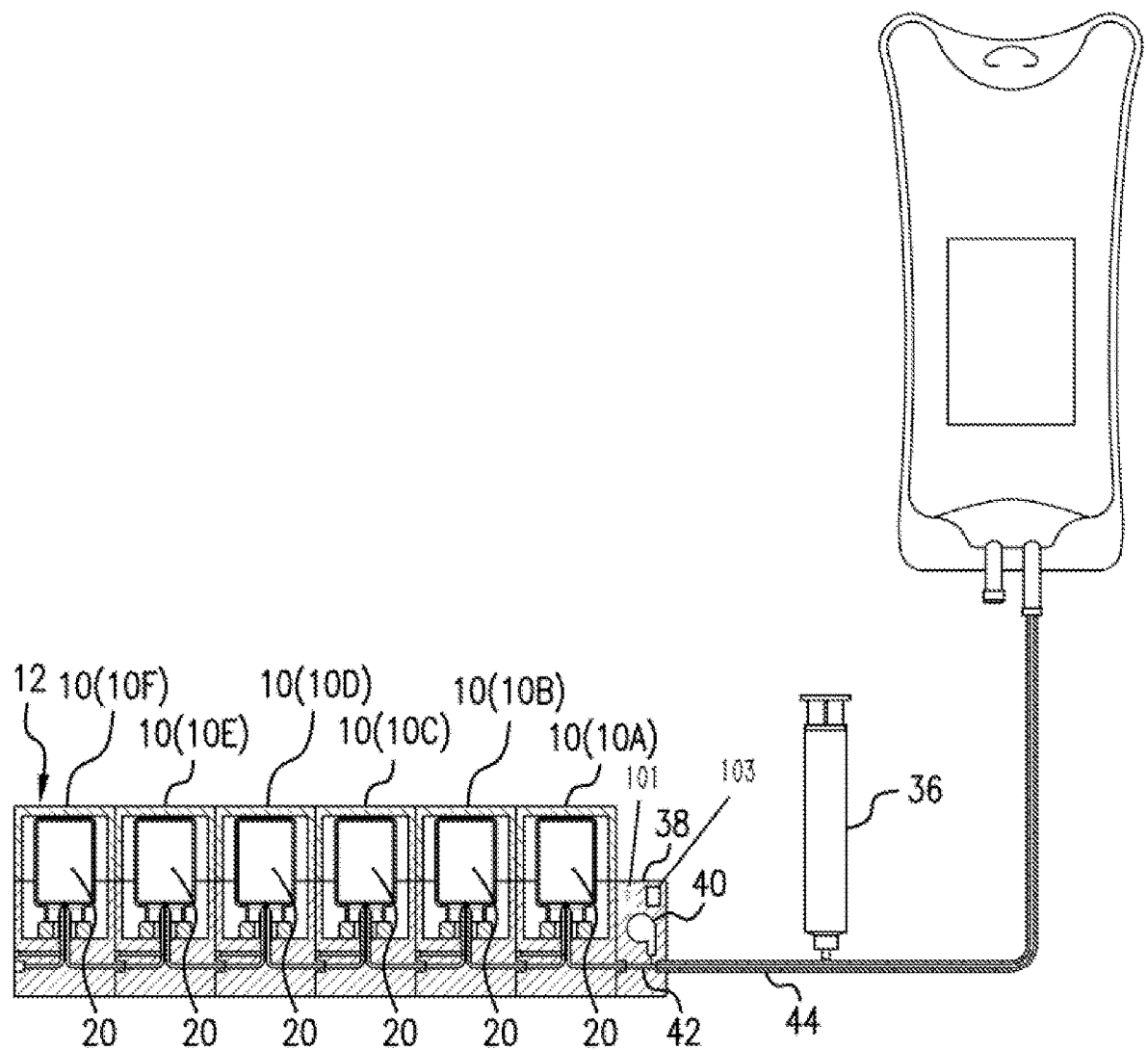

The modules 10 are formed to be serially connected so that the primary and secondary passageways 32, 34 of adjacent modules 10 are in communication, as shown in FIGS. 3 and 7. In particular, the modules 10 are serially connected so that, with the exception of the ultimate module (marked as 10F in FIG. 3), the primary passageway 32 of each module 10 is in communication with the secondary passageway 34 of the adjacent module. For the ultimate module 10F, the primary passageway 32 is left open as not being connected to a further module. The primary passageway 32 of the ultimate module 10F may be plugged or otherwise closed off.

As shown in FIG. 3, liquid may be drawn from the drug vials 20 to be delivered through a single discharge in the form of the secondary passageway 34 of the first located module (marked as 10A in FIG. 3). This allows for different liquid drugs to be accommodated by the drug vials 20 of the modules 10A-10F with the liquid drugs being combined by the device 12. As will be appreciated by those skilled in the art, any quantity of the modules 10 may be utilized, possibly limited by the fluidic resistance of the assembly and/or strength of negative pressure utilized with the assembly.

A source of negative pressure may be used to draw the liquid drugs through the modules 10. Negative pressure may be provided by an external pump or syringe 36 in communication (directly or indirectly) with the secondary passageway 34 of the first module 10A. A housing 38 may be provided with the device 12 which may contain a pump 40, e.g., electrically powered. The internal pump 102 may be provided in the housing 102, along with any motor, power source 101, controller 103, etc., useable to operate and/or control the pump 40. The housing 38 may be provided with discharge passageway 42 in communication with the secondary passageway 34 of the first module 10A. The discharge passageway 42 may be subjected to negative pressure by the external pump or syringe 36 and/or the pump 40. Discharge tubing 44 may be provided in communication with the discharge passageway 42 to convey discharged liquid drug to a target delivery site, such as an IV bag, drug container, or directly into a patient. A cannula, as known in the art, may be provided on the discharge tubing 44 as needed for injection or other accessing. Sufficient negative pressure needs to be generated to draw fully the contents of all of the drug vials 20. Check valving may be provided along the discharge passageway 42 and/or the discharge tubing 44 to limit back flow. The external pump 36 and/or the pump 40 may be non-contact pumps, e.g., peristaltic pumps, which may act on the discharge passageway 42 or the discharge tubing 40 without contacting liquid flow therethrough.

With the drug vials 20 being rigid (e.g., glass or polymeric construction), the device 12 may require venting to facilitate acceptable liquid flow throughout the device 12. Preferably, each of the modules 10 is provided with a venting passageway 46 in communication with the primary passageway 32. The venting passageway 46 extends through exterior surface 48 of the body 14 to terminate at vent opening 50. The vent opening 50 is positioned so as to be covered fully by an adjacent module with the module being serially connected to a further module (e.g., the vent opening 50 of the first module 10A is fully covered by the body 14 of the second module 10B with the vent opening 50 of the second module 10B being covered by the body 14 of the third module 10C, and so forth). The vent opening 50 of the ultimate module 10F is exposed without being covered. This allows for venting for the device 12 from the end of the series of connected modules 10. To limit ingress of contaminants, each of the vent openings 50 may be provided with an aseptic particulate filter 51, which allows transmission therethrough of air, but resists passage of microbes or other contaminants.

The primary and secondary passageways 32, 34 may be provided with male and female configurations to provide for fitted connections. The Figures show each of the secondary passageways 34 terminating as a protruding boss 52 formed to be insertingly received in a socket 54 defined at the opening to the primary passageways 32. These components may be reversed with the bosses 52 protruding from the primary passageways 32 and the sockets 54 being formed in the openings of the secondary passageways 34. In either configuration, elastomeric seals or other components (such as o-rings) may be provided on the bosses 52 and/or the sockets 54 to enhance the frictional connection and the liquid-tight connection at the interface therebetween. Friction may be relied upon for maintaining connections between the modules 10. As shown in FIGS. 6-7, the boss and the socket may be configured as mating male and female luer components. Check valving may be utilized to seal the primary and secondary passageways 32, 34 prior to use. Connection of the modules 10 may cause the opening of the check valving.

To limit reusability of the modules 10, the bosses 52 and the sockets 54 may be formed to lock together when assembled. For example, as shown in FIG. 8A, the bosses 52 may be each formed with a protruding ridge 53 formed to snap engage corresponding channel 55 formed in each of the sockets 54. The ridges 53 and the channels 55 may be ramped to restrict reverse movement of the bosses 52, relative to the sockets 54, once sufficiently inserted therein. In addition, or alternatively, cooperating locking elements may be provided on the modules 10, outside of the bosses 52 and the sockets 54 which lock together with assembly of the modules 10. It is preferred that the locking occur along the flow path, such as locking between the bosses 52 and the sockets 54, so that attempts to un-do the locked engagement results in damage along the flow path, thereby rendering the modules 10 unuseable.

Figure 5:
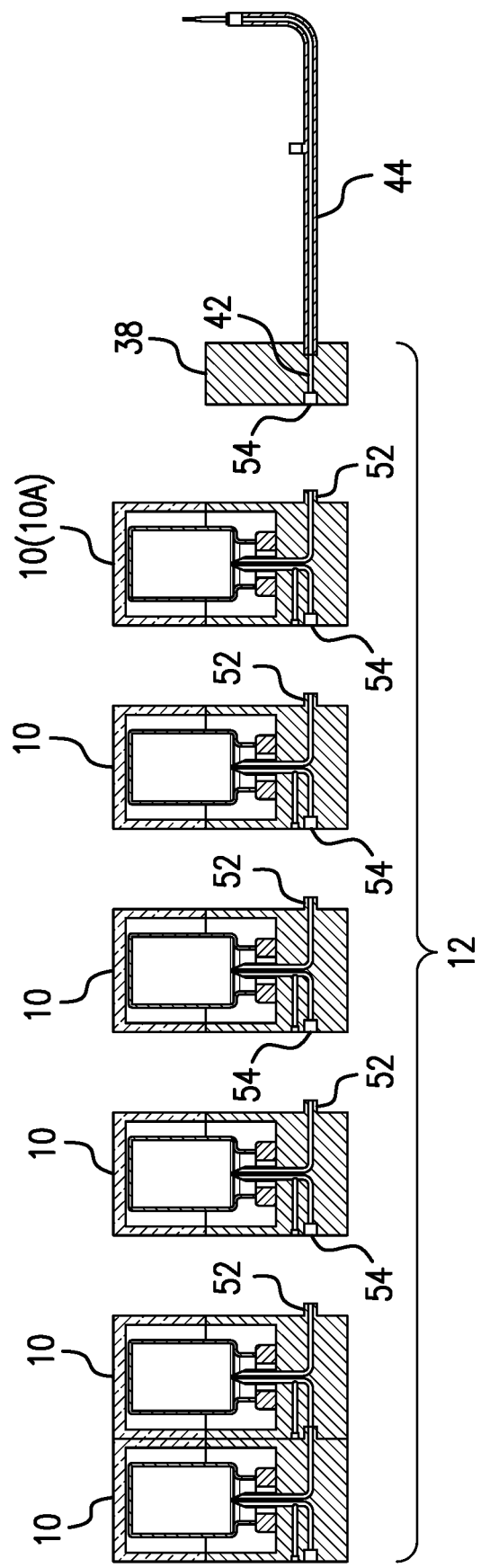

The housing 38 may be provided with a feature to cooperate with the secondary passageway 34 of the first module 10A, such as the socket 54 (FIG. 5).

As shown in FIG. 8, in an alternative arrangement, the venting passageway 46 may not be provided. To allow for venting, a venting module 56 may be provided formed to be mounted to the primary passageway 32 of the ultimate module. The venting module 56 includes an aseptic particulate filter to allow for air flow therethrough with limiting ingress of contaminants.

To best preserve the sterility of the module 10 and the contents of the drug vial 20 during shipping and storage, the drug vial 20 may be provided intact, not breached by the cannula 22. As such, it is preferred that the drug vial 20 be maintained in a spaced relationship from the cannula 22, until use. To provide for this arrangement, the vial retainer 16 may be formed to snap engage or otherwise retain the drug vial 20 such that the drug vial 20 is displaceable with the vial retainer 16 (e.g., the vial retainer 16 may include grippers 64 or a collar 68 formed to retentively engage a portion of the drug vial 20, such as about a neck N of the drug vial 20). Displacement of the vial retainer 16, with the drug vial 20, relative to the cannula 22 may be utilized to cause the cannula 22 to breach the septum 24 when ready for use. In addition, the septum 24 of the drug vial 20 may be covered with a removable barrier 70 formed to limit contamination of the septum 24, e.g., the removable barrier 70 being a microbial barrier as is known in the art. In this manner, the drug vial 20 may be better maintained in a sterile state.

Figure 9A:
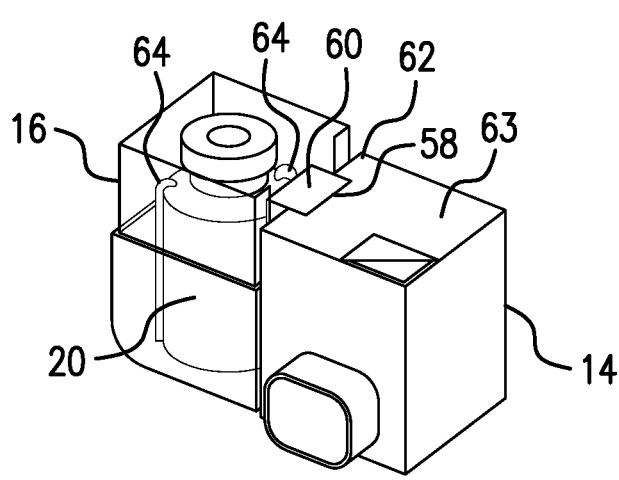
FIGS. 9A-9D depict a sliding hinge arrangement usable with the subject invention.
Figure 9B:
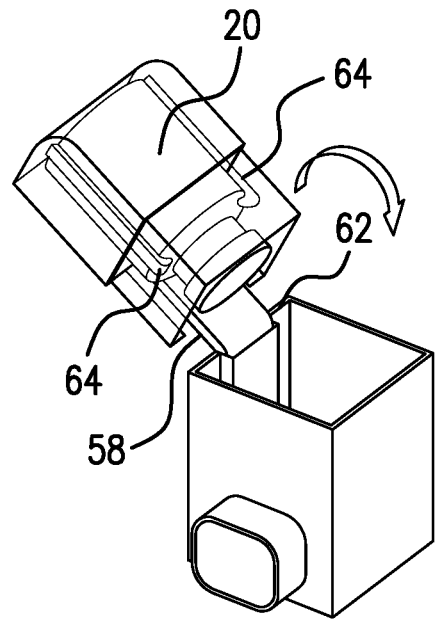
Figure 9C:
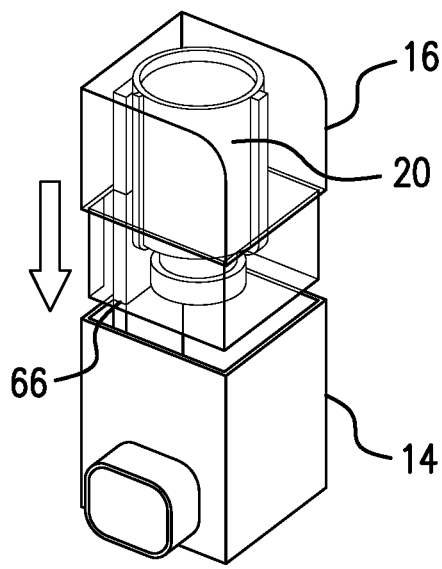
Figure 9D:
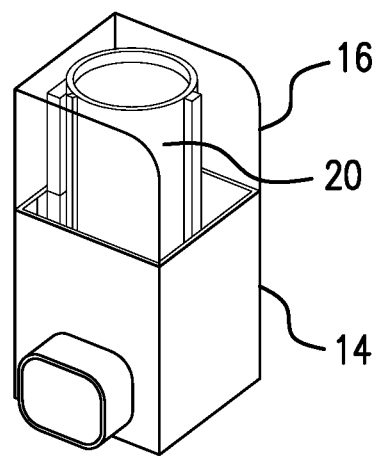

For example, as shown in FIGS. 9A-9D, to achieve displacement of the vial retainer 16 relative the body 14, a sliding hinge 58 may be provided connecting the vial retainer 16 to the body 14 for each module 10. As shown in FIG. 9A, the sliding hinge 58 has first end 60 hingedly connected to top edge 62 of the body 14. It is preferred that the vial retainer 16 be formed to accommodate the drug vial 20 in an initial state (FIG. 9A). The grippers 64 may be provided with the vial retainer 16 to hold the drug vial 20 during loading. Initially, the module 10 may be in an open state as shown in FIG. 9A with a sterile barrier 63 covering the cannula 22 within the body 14. In a first step, with the drug vial 20 loaded in the grippers 64 of the vial retainer 16, the sterile barrier 63 is removed. If the removable barrier 70 is not provided with the drug vial 20, the septum 24 is preferably wiped with an antiseptic wipe to provide sterilization of the outer surface of the septum 24. The vial retainer 16, with the contained drug vial 20, is caused to be displaced by rotation with the sliding hinge 58 about the top edge 62 (FIG. 9B) to the position shown in FIG. 9C. The sliding hinge 58 has an elongated plate shape which extends from the first end 60. Once in the up position as shown in FIG. 9C, the sliding hinge 58 is caused to translate into recessed channel 66 formed in the body 14. This straight-line motion causes the vial retainer 16 to be lowered into the body 14, with the drug vial 20, sufficiently such that the cannula 22 fully pierces the septum 24 (FIG. 9D). Locking elements may be provided to lock the vial retainer 16 to the body 14 once the septum 24 has been breached.

As will be appreciated by those skilled in the art, the vial retainer 16 may be displaced in various manners relative to the body 14 to allow for the cannula 22 to pierce the septum 24. With reference to FIGS. 10A-10D, the vial retainer 16 may be slidable relative to the body 14. This allows for a shipping/storage position shown in FIG. 10A, where the septum 24 is separated from the cannula 22. To prepare the module 10, the vial retainer 16 is displaced relative to the body 14 by being axially slid outwardly from the body 14. The vial retainer 16 may be yoke-shaped with arms 72 translating along channels formed in the body 14. Stops are preferably provided along the channels to prevent the vial retainer 16 from being completely pulled out of the body 14. In addition, a releasable locking arrangement may be provided to initially maintain the vial retainer 16 in a fixed position, relative to the body 14, in the shipping/transportation position shown in FIG. 10A. The releasable locking arrangement may be: a frangible connection between the vial retainer 16 and the body 14 (e.g., breakable fused or adhesive connection); mechanical fixation (e.g., ramped and/or depressed interengagement which resists movement of the vial retainer 16 relative to the body 14); and/or, an external packaging (e.g., tape or shrink-wrap packaging formed to restrict relative movement between the vial retainer 16 and the body 14).

Figure 10A:
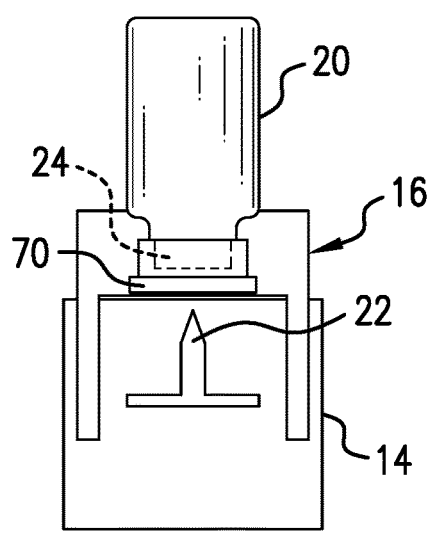
FIGS. 10A-10D depict a slidable vial retainer usable with the subject invention.
Figure 10B:
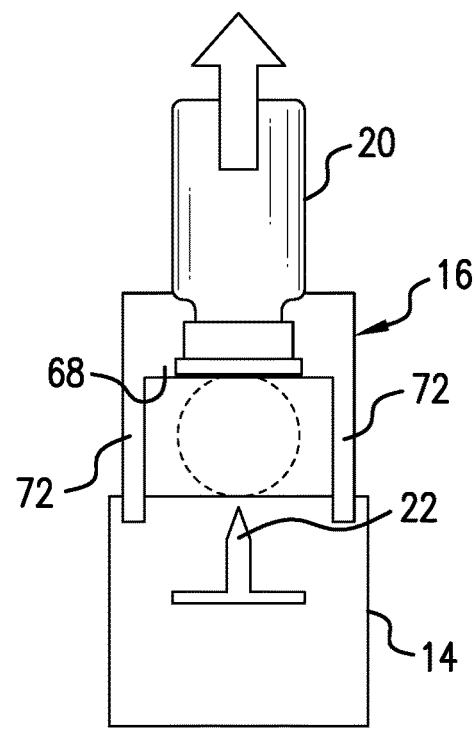
Figure 10C:
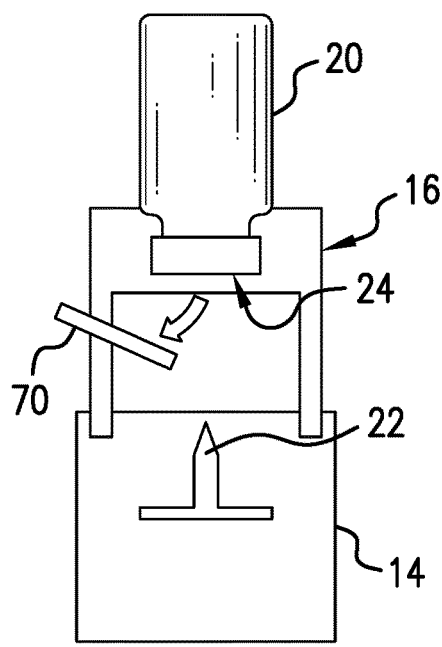
Figure 10D:
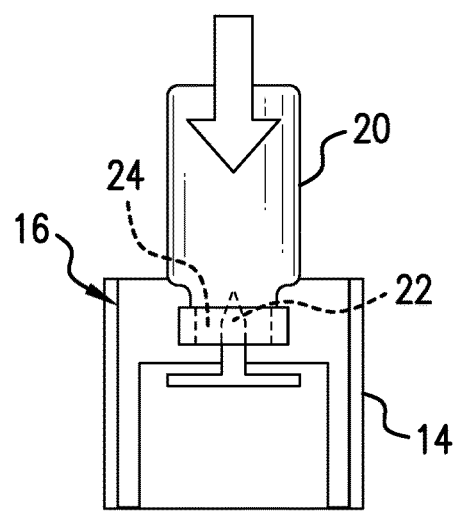

The arms 72 are preferably provided with sufficient length to allow a user to access to the septum 24, as shown in FIG. 10B, with the vial retainer 16 pulled away from the body 14. As shown in FIG. 10C, this allows for removal of the removable barrier 70, if present. In addition, this allows for wiping the septum 24 with an antiseptic wipe, if necessary. In addition, the body 14 may be covered by the sterile barrier 63. Access to the sterile barrier 63 is also provided to permit removal thereof with vial retainer 16 being in the displaced position as shown in FIG. 10C. With all barriers 63, 70 removed and/or antiseptic wiping completed, the vial retainer 16 is displaced by axially sliding the vial retainer 16 into the body 14 so that the cannula 22 pierces the septum 24, as shown in FIG. 10D. Detents or other locking elements may be provided to retain the vial retainer 16 in the state shown in FIG. 10D to limit outward sliding of the vial retainer 16.

Figure 11A:
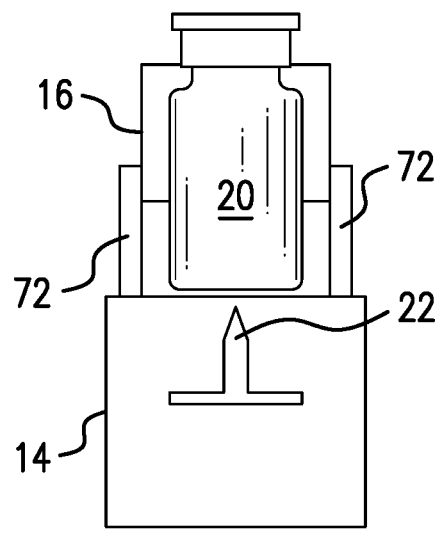
FIGS. 11A-11D depict a rotatable vial retainer, having the vial initially facing upwardly, usable with the subject invention.
Figure 11B:
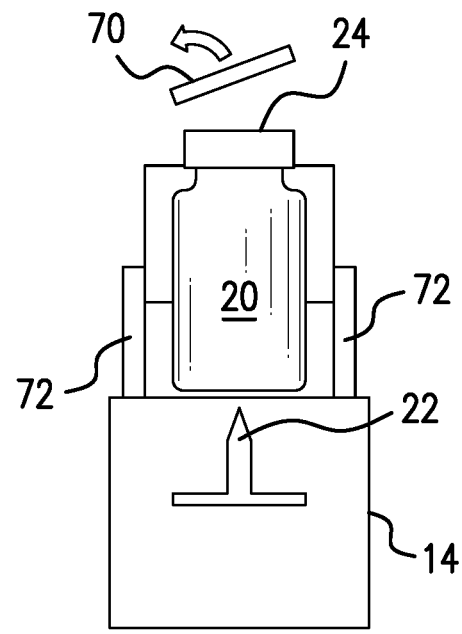
Figure 11C:
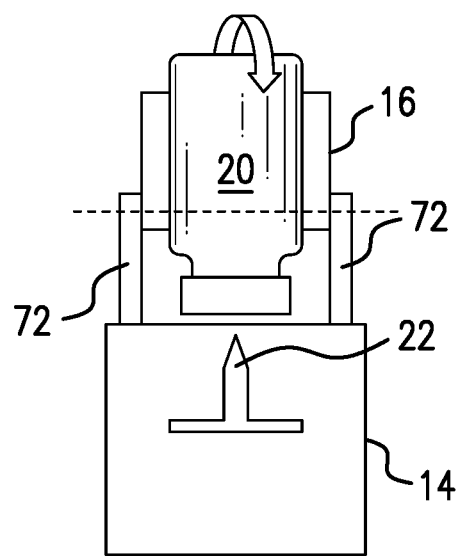
Figure 11D:
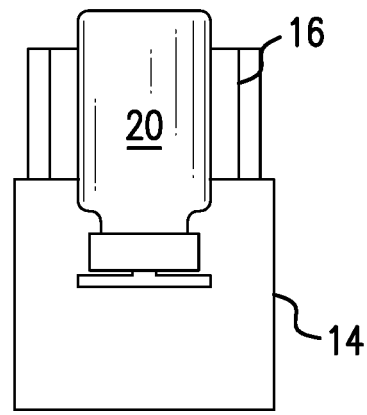

With reference to FIGS. 11A-11D, the vial retainer 16 of the prior embodiment may be modified to have the septum 24 initially exposed, as shown in FIG. 11A. This allows for the septum 24 to be readied without any adjustment of the drug vial 20. Once readied, the vial retainer 16 is provided with a rotatable connection with the drug vial 20, whereby the drug vial 20 may be rotated to align the septum 24 with the cannula 22 (e.g., 180 degree rotation). Thereafter, as with the prior embodiment, the vial retainer 16 is urged into the body 14 to have the cannula 22 pierce the septum 24.

Figure 12A:
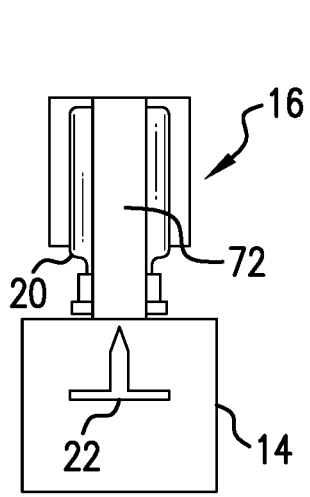
FIGS. 12A-12E depict a rotatable vial retainer, having the vial initially facing downwardly, usable with the subject invention.
Figure 12B:
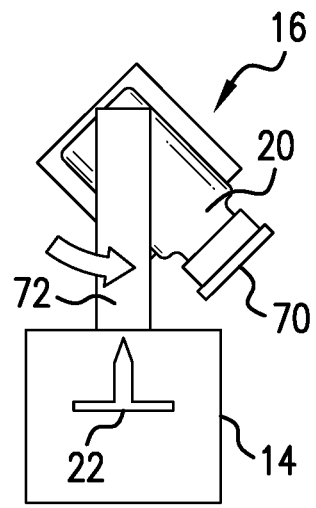
Figure 12C:
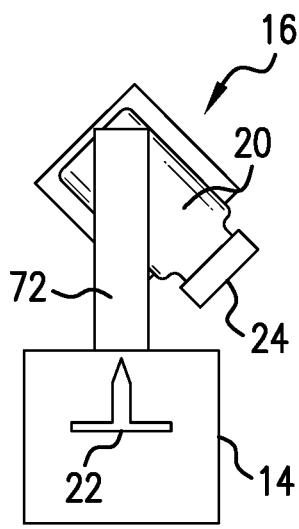
Figure 12D:
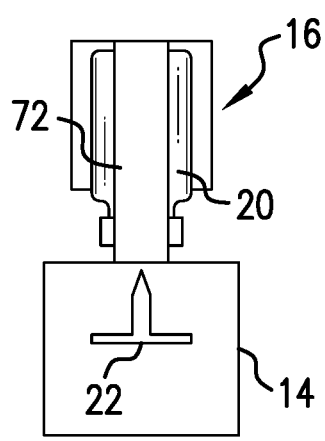
Figure 12E:
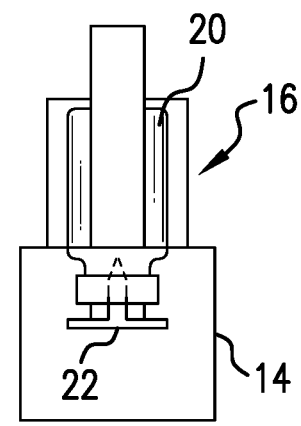

In a further possible modification, as shown in FIGS. 12A-12E, the drug vial 20 may be provided with the septum 24 facing the body 14, in the same manner as in FIG. 10A. The rotatable connection between the vial retainer 16 and the drug vial 20 in this embodiment may be used to expose the septum 24 (FIG. 12B) to allow the septum 24 to be readied (FIG. 12C). Thereafter, the drug vial 20 is returned to its initial state (FIG. 12D) and urged into the body 14 for engagement with the cannula 22.

Figure 13A:
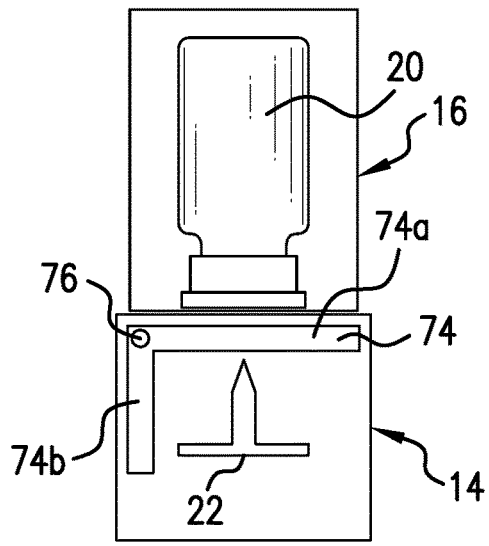
FIGS. 13A-13D depict a slidable vial retainer usable with the subject invention.

With reference to FIGS. 13A-13D, a further manner of displacing the vial retainer 16 relative to the body 14 is shown. In particular, the body 14 may be provided with at least one channel 74 in which detent 76, located on the vial retainer 16, axially slides. The interengagement between the channel 74 and the detent 76 constrains the movement of the vial retainer 16 relative to the body 14. The channel 74 may be L-shaped, having a horizontal portion 74a, aligned for transverse movement of the vial retainer 16 relative to the body 14, and a vertical portion 74b, aligned for coaxial movement of the vial retainer 16 relative to the body 14. As shown in FIG. 13A, the detent 76 of the vial retainer 16 is initially located in the horizontal portion 74a of the channel 74. The horizontal portion 74a is positioned so that, with the detent 76 seated in the horizontal portion 74a, the septum 24 is spaced from the cannula 22. This allows for shipping and storage with the septum 24 being spaced from the cannula 22. A releasable locking arrangement may be provided to maintain the detent 76 in a fixed position in the horizontal portion 74a. The releasable locking arrangement may be: a frangible connection between the detent 76 and the channel 74 (e.g., breakable fused or adhesive connection); mechanical fixation (e.g., ramped and/or depressed interengagement which resists movement of the detent 76 along the channel 74); and/or, an external packaging (e.g., tape or shrink-wrap packaging formed to restrict relative movement between the vial retainer 16 and the body 14).

Figure 13B:
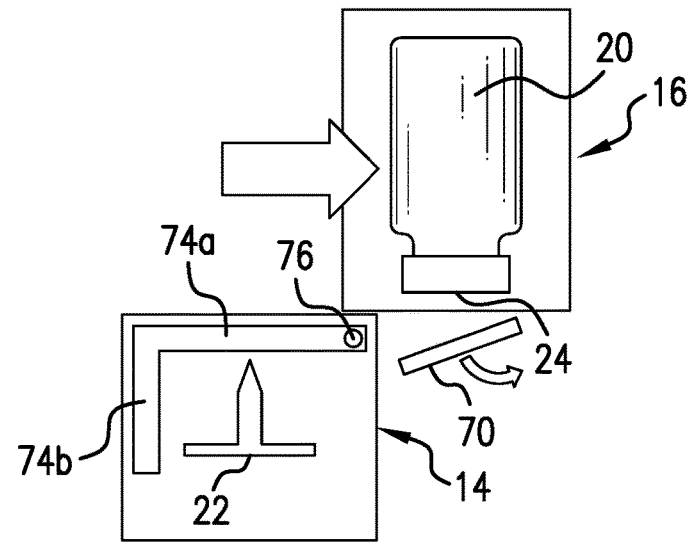
Figure 13C:
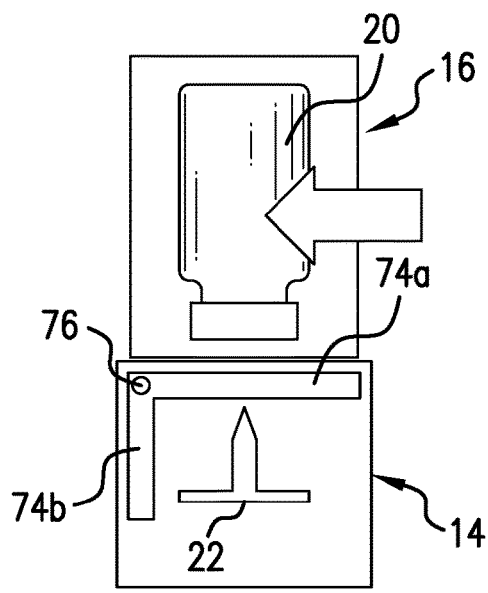
Figure 13D:
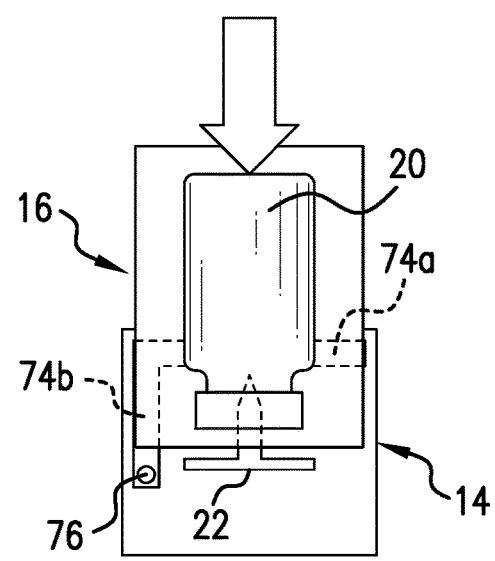

To ready the module 10, the vial retainer 16 is caused to move transversely along the horizontal portion 74a, as shown in FIG. 13B. It is preferred that the detent 76 is located along one side of the vial retainer 16 to allow for the vial retainer 16 to be sufficiently shifted out of alignment with the body 14 to expose the septum 24. The detent 76 may be formed on a downward depending arm protruding from the vial retainer 16. With the septum 24 exposed, as shown in FIG. 13B, the removable barrier 70 may be removed and/or the septum 24 may be wiped. In addition, the body 14 may be readied, e.g., removal of the sterile barrier 63. Once readied, the vial retainer 16 is shifted back along the horizontal portion 74a until the detent 76 is in alignment with the vertical portion 74b, as shown in FIG. 13C. Thereafter, the vial retainer 16 is urged axially into the body 14, with the detent 16 sliding along the vertical portion 74b, and with the cannula 22 piercing the septum 24. The vertical portion 74b must be provided with sufficient length to ensure that the cannula 22 fully pierces the septum 24 in accessing the drug contents of the drug vial 20. Detents or other locking elements may be provided to retain the vial retainer 16 in the state shown in FIG. 13D to limit outward sliding of the vial retainer 16.

Figure 14A:
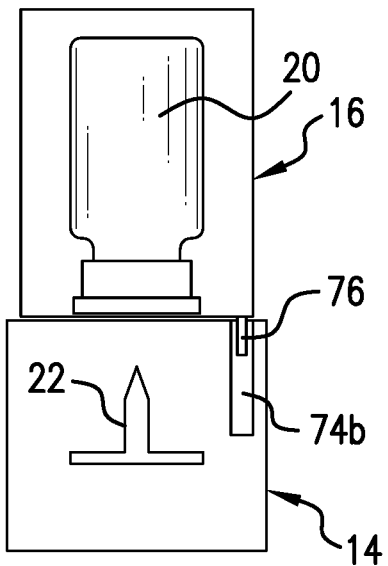
FIGS. 14A-14D depict a further rotatable vial retainer usable with the subject invention.
Figure 14B:
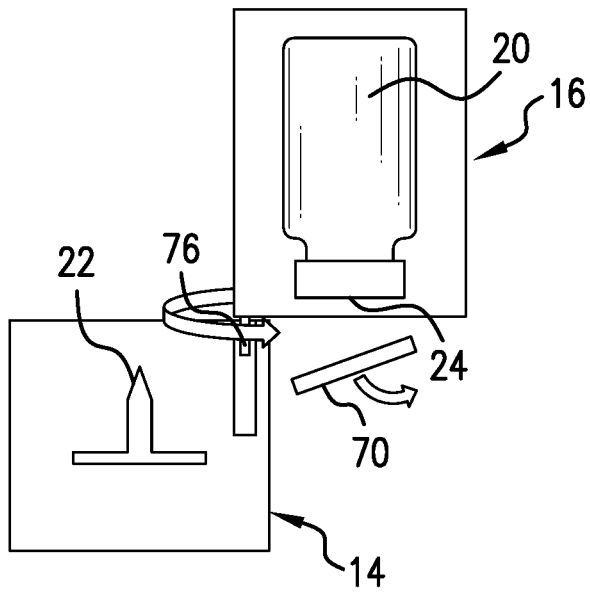
Figure 14C:
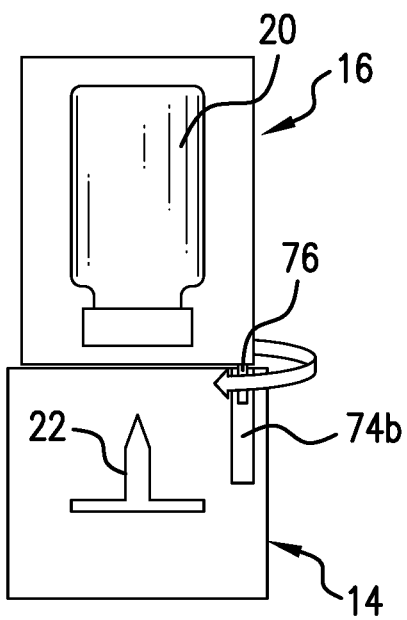
Figure 14D:
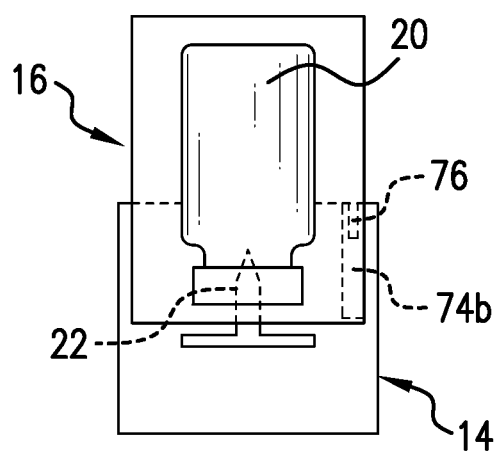

With reference to FIGS. 14A-14D, the embodiment of FIGS. 13A-13D may be modified to have the detent 76 provide a rotatable connection between the vial retainer 16 and the body 14. In this embodiment, the horizontal portion 74a is not required. With reference to FIG. 14A, the vial retainer 16 is positioned relative to the body 14 in similar manner to the previous embodiment. A releasable locking arrangement may be likewise provided to restrict pre-use movement of the vial retainer 16 relative to the body 14. As shown in FIG. 14B, the septum 24 is exposed by rotating the vial retainer 16 relative to the body 14 about the detent 74. Once the septum 24 and the body 14 are readied, as described above, the vial retainer 16 is rotated back into alignment with the body 14, as shown in FIG. 14C. Thereafter, the vial retainer 16 is urged axially into the body 14, with the detent 16 sliding along the vertical portion 74b, and with the cannula 22 piercing the septum 24. As with the prior embodiment, the vertical portion 74b must be provided with sufficient length to ensure that the cannula 22 fully pierces the septum 24 in accessing the drug contents of the drug vial 20. Detents or other locking elements may be provided to retain the vial retainer 16 in the state shown in FIG. 14D to limit outward sliding of the vial retainer 16.

Figure 15A:
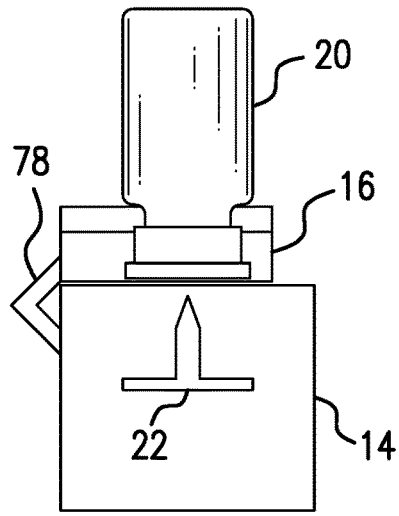
FIGS. 15A-15D depict a vial retainer connected to the body of the module by a living hinge or tether in accordance with the subject invention.
Figure 15B:
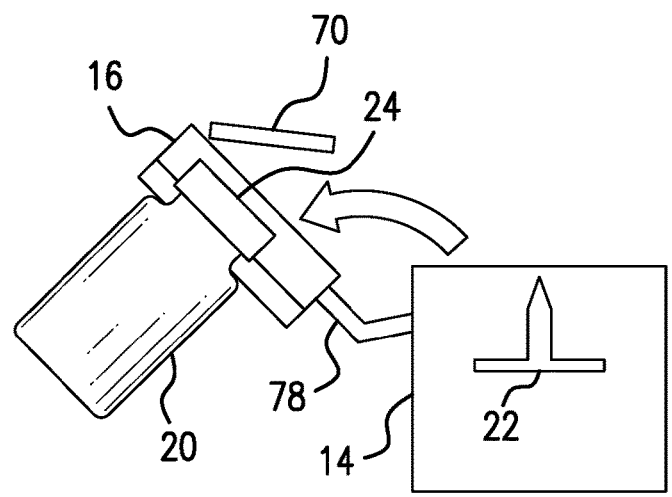

With reference to FIGS. 15A-15D, in a further embodiment, the vial retainer 16 may be connected to the body 14 by a living hinge or tether 78. Here, the vial retainer 16 may be formed as a block formed for guided sliding within the body 14. The living hinge or tether 78 may be integrally formed with the vial retainer 16 and/or the body 14 (e.g., being made of polymeric material). As shown in FIG. 15A, in a transportation/shipping state, the vial retainer 16 may be removably affixed to the body, such as by a frangible connection (fused and/or adhesive) and/or by external packaging. To ready for use, as shown in FIG. 15B, the vial retainer 16 may be separated from the body 14 to allow access to the septum 24. The living hinge or tether 78 maintains a connection between the vial retainer 16 and the body 14. The living hinge or tether 78 may be formed with a length and rigidity which permits supporting the vial retainer 16, with the drug vial 20, in a separated state from the body 14. This permits the vial retainer 16 to be maintained in a supported position relative to the body 14.

Figure 15C:
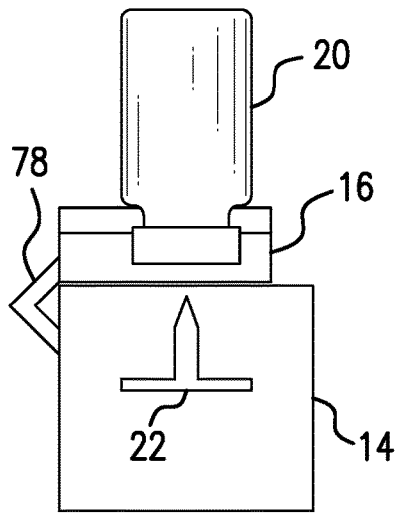
Figure 15D:
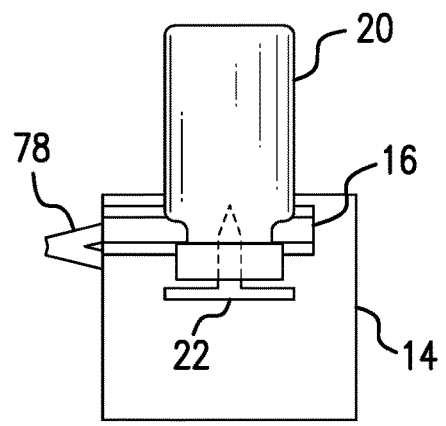

Once the septum 24 and the body 14 have been readied, the vial retainer 16 may be aligned with the body 14, as shown in FIG. 15C. Thereafter, the vial retainer 16 is urged into the body 14 to allow the cannula 22 to pierce the septum 24, in similar manner to the embodiments discussed above. The living hinge or tether 78 is provided with sufficient flexibility to allow for sufficient displacement of the vial retainer 16 relative to the body 14 for the cannula 22 to fully pierce the septum 24. FIGS. 15C and 15D show the cannula 22 piercing a portion of the vial retainer 16. These are schematic representations. It is preferred that the cannula 22 not pierce a portion of the vial retainer 16. The vial retainer 16 may be formed with portions surrounding the septum 24, including downward extending portions to provide rigidity to the vial retainer 16 without obscuring the septum 24.

For all embodiments described herein, the cannula 22 is sterilized prior to use, along with all liquid flow paths of the module 10. The sterile barrier 63 and the removable barrier 70 are used to maintain sterility of the module 10, including the drug vial 20, during shipping and storage. As such, the sterile barrier 63 and/or the removable barrier 70 may be used with any of the embodiments disclosed herein. In addition, other protective packaging, such as being packaged in a pouch, may be utilized.

As will be appreciated by those skilled in the art, the housing 38 may be provided with various controls and systems, such as a microprocessor to record use details and a wireless transmitter to transmit such details.

One or more of the drug vials 20 may contain lyophilized drug which may be reconstituted with introduction of a diluent. A diluent may be located upstream from the lyophilized drug such that the diluent is drawn into the drug vial with the lyophilized drug with reconstituted drug being drawn therefrom. Various drugs may be contained in the drug vials 20. Diluents or other additives may be contained as well to increase the efficacy of the drug combination to be delivered. For example, as shown in FIG. 17, inlet tubing 100 from reservoir 102 may be connected to the socket 54 of the ultimate module 10F. This allows for a reservoir of diluent to be provided for the device 12, particularly to allow for flow through all of the modules 10. The reservoir 102 preferably is a flexible bag, which is collapsible with the withdrawal of diluent therefrom. This allows for the device 10 to minimize the need for venting, possibly altogether eliminating the need for venting. If venting is required, the particulate filter 51 may be provided on the ultimate module 10F. The diluent may be used for reconstitution of drug components in the modules 10. In addition, the diluent may contain drug components to further enhance the combinatorial effect of the device 12. It is also possible to provide the reservoir 102 gravitationally higher (e.g., by suspending) than the device 12 so that head is generated to assist flow of the diluent through the device 12.

In one embodiment, the drug delivery device 12 is able to deliver two or more drugs for the benefit of the patient suffering from any of a wide range of diseases or conditions, e.g., cancer, autoimmune disorder, inflammatory disorder, cardiovascular disease or fibrotic disorder.

In one embodiment, one or more of the drugs of the drug delivery device 12 is an immune checkpoint inhibitor. In certain embodiments, the immune checkpoint inhibitor is Programmed Death-1 ("PD-1") pathway inhibitor, a cytotoxic T-lymphocyte-associated antigen 4 ("CTLA-4") antagonist, a Lymphocyte Activation Gene-3 ("LAG3") antagonist, a CD80 antagonist, a CD86 antagonist, a T cell immunoglobulin and mucin domain ("Tim-3") antagonist, a T cell immunoreceptor with Ig and ITIM domains ("TIGIT") antagonist, a CD20 antagonist, a CD96 antagonist, a Indoleamine 2,3-dioxygenase ("IDO1") antagonist, a stimulator of interferon genes ("STING") antagonist, a GARP antagonist, a CD40 antagonist, Adenosine A2A receptor ("A2aR") antagonist, a CEACAM1 (CD66a) antagonist, a CEA antagonist, a CD47 antagonist, a Receptor Related Immunoglobulin Domain Containing Protein ("PVRIG") antagonist, a tryptophan 2,3-dioxygenase ("TDO") antagonist, a V-domain Ig suppressor of T cell activation ("VISTA") antagonist, or a Killer-cell Immunoglobulin-like Receptor ("KIR") antagonist.

In one embodiment, the PD-1 pathway inhibitor is an anti-PD-1 antibody or antigen binding fragment thereof. In certain embodiments, the anti-PD-1 antibody is pembrolizumab (KEYTRUDA; MK-3475), pidilizumab (CT-011), nivolumab (OPDIVO; BMS-936558), PDR001, MEDI0680 (AMP-514), TSR-042, REGN2810, JS001, AMP-224 (GSK-2661380), PF-06801591, BGB-A317, BI 754091, or SHR-1210.

In one embodiment, the PD-1 pathway inhibitor is an anti-PD-L1 antibody or antigen binding fragment thereof. In certain embodiments, the anti-PD-L1 antibody is atezolizumab (TECENTRIQ; RG7446; MPDL3280A; RO5541267), durvalumab (MEDI4736), BMS-936559, avelumab (bavencio), LY3300054, CX-072 (Proclaim-CX-072), FAZ053, KN035, or MDX-1105.

In one embodiment, the PD-1 pathway inhibitor is a small molecule drug. In certain embodiments, the PD-1 pathway inhibitor is CA-170. In another embodiment, the PD-1 pathway inhibitor is a cell based therapy. In one embodiment, the cell based therapy is a MiHA-loaded PD-L1/L2-silenced dendritic cell vaccine. In other embodiments, the cell based therapy is an anti-programmed cell death protein 1 antibody expressing pluripotent killer T lymphocyte, an autologous PD-1-targeted chimeric switch receptor-modified T lymphocyte, or a PD-1 knockout autologous T lymphocyte.

In one embodiment, the PD-1 pathway inhibitor is an anti-PD-L2 antibody or antigen binding fragment thereof. In another embodiment, the anti-PD-L2 antibody is rHIgM12B7.

In one embodiment, the PD-1 pathway inhibitor is a soluble PD-1 polypeptide. In certain embodiments, the soluble PD-1 polypeptide is a fusion polypeptide. In some embodiments, the soluble PD-1 polypeptide comprises a ligand binding fragment of the PD-1 extracellular domain. In other embodiments, the soluble PD-1 polypeptide comprises a ligand binding fragment of the PD-1 extracellular domain. In another embodiment, the soluble PD-1 polypeptide further comprises an Fc domain.

In one embodiment, the immune checkpoint inhibitor is a CTLA-4 antagonist. In certain embodiments, the CTLA-4 antagonist is an anti-CTLA-4 antibody or antigen binding fragment thereof. In some embodiments, the anti-CTLA-4 antibody is ipilimumab (YERVOY), tremelimumab (ticilimumab; CP-675,206), AGEN-1884, or ATOR-1015. In one embodiment, the drug delivery device 12 includes a CTLA-4 antagonist, e.g., ipilimumab (YERVOY), a PD-1 pathway inhibitor, e.g., nivolumab (OPDIVO) or pembrolizumab (KEYTRUDA).

In one embodiment, the immune checkpoint inhibitor is an antagonist of LAG3. In certain embodiments, the LAG3 antagonist is an anti-LAG3 antibody or antigen binding fragment thereof. In certain embodiments, the anti-LAG3 antibody is relatlimab (BMS-986016), MK-4280 (28G-10), REGN3767, GSK2831781, IMP731 (H5L7BW), BAP050, IMP-701 (LAG-5250), IMP321, TSR-033, LAG525, BI 754111, or FS-118. In one embodiment, the drug delivery device 12 includes a LAG3 antagonist, e.g., relatlimab or MK-4280, and a PD-1 pathway inhibitor, e.g., nivolumab (OPDIVO) or pembrolizumab (KEYTRUDA). In one embodiment, the drug delivery device 12 includes a LAG3 antagonist, e.g., relatlimab or MK-4280, and a CTLA-4 antagonist, e.g., ipilimumab (YERVOY). In one embodiment, the drug delivery device 12 includes a LAG3 antagonist, e.g., relatlimab or MK-4280, a CTLA-4 antagonist, e.g., ipilimumab (YERVOY), and a PD-1 pathway inhibitor, e.g., nivolumab (OPDIVO) or pembrolizumab (KEYTRUDA).

In one embodiment, the CTLA-4 antagonist is a soluble CTLA-4 polypeptide. In one embodiment, the soluble CTLA-4 polypeptide is abatacept (ORENCIA), belatacept (NULOJIX), RG2077, or RG-1046. In another embodiment, the CTLA-4 antagonist is a cell based therapy. In some embodiments, the CTLA-4 antagonist is an anti-CTLA4 mAb RNA/GITRL RNA-transfected autologous dendritic cell vaccine or an anti-CTLA-4 mAb RNA-transfected autologous dendritic cell vaccine.

In one embodiment, the immune checkpoint inhibitor is a KIR antagonist. In certain embodiments, the KIR antagonist is an anti-KIR antibody or antigen binding fragment thereof. In some embodiments, the anti-KIR antibody is lirilumab (1-7F9, BMS-986015, IPH 2101) or IPH4102.

In one embodiment, the immune checkpoint inhibitor is TIGIT antagonist. In one embodiment, the TIGIT antagonist is an anti-TIGIT antibody or antigen binding fragment thereof. In certain embodiments, the anti-TIGIT antibody is BMS-986207, AB 154, COM902 (CGEN-15137), or OMP-313M32.

In one embodiment, the immune checkpoint inhibitor is Tim-3 antagonist. In certain embodiments, the Tim-3 antagonist is an anti-Tim-3 antibody or antigen binding fragment thereof. In some embodiments, the anti-Tim-3 antibody is TSR-022 or LY3321367.

In one embodiment, the immune checkpoint inhibitor is an IDOL antagonist. In another embodiment, the IDO1 antagonist is indoximod (NLG8189; 1-methyl-D-TRP), epacadostat (INCB-024360, INCB-24360), KHK2455, PF-06840003, navoximod (RG6078, GDC-0919, NLG919), BMS-986205 (F001287), or pyrrolidine-2,5-dione derivatives.

In one embodiment, the immune checkpoint inhibitor is a STING antagonist. In certain embodiments, the STING antagonist is 2' or 3'-mono-fluoro substituted cyclic-di-nucleotides; 2'3'-di-fluoro substituted mixed linkage 2',5'-3', 5' cyclic-di-nucleotides; 2'-fluoro substituted, bis-3',5' cyclic-di-nucleotides; 2',2"-diF-Rp,Rp,bis-3',5' cyclic-di-nucleotides; or fluorinated cyclic-di-nucleotides.

In one embodiment, the immune checkpoint inhibitor is CD20 antagonist. In some embodiments, the CD20 antagonist is an anti-CD20 antibody or antigen binding fragment thereof. In one embodiment, the anti-CD20 antibody is rituximab (RITUXAN; IDEC-102; IDEC-C2B8), ABP 798, ofatumumab, or obinutuzumab.

In one embodiment, the immune checkpoint inhibitor is CD80 antagonist. In certain embodiments, the CD80 antagonist is an anti-CD80 antibody or antigen binding fragment thereof. In one embodiment, the anti-CD80 antibody is galiximab or AV 1142742.

In one embodiment, the immune checkpoint inhibitor is a GARP antagonist. In some embodiments, the GARP antagonist is an anti-GARP antibody or antigen binding fragment thereof. In certain embodiments, the anti-GARP antibody is ARGX-115.

In one embodiment, the immune checkpoint inhibitor is a CD40 antagonist. In certain embodiments, the CD40 antagonist is an anti-CD40 antibody for antigen binding fragment thereof. In some embodiments, the anti-CD40 antibody is BMS3h-56, lucatumumab (HCD122 and CHIR-12.12), CHIR-5.9, or dacetuzumab (huS2C6, PRO 64553, RG 3636, SGN 14, SGN-40). In another embodiment, the CD40 antagonist is a soluble CD40 ligand (CD40-L). In one embodiment, the soluble CD40 ligand is a fusion polypeptide. In one embodiment, the soluble CD40 ligand is a CD40-L/FC2 or a monomeric CD40-L.

In one embodiment, the immune checkpoint inhibitor is an A2aR antagonist. In some embodiments, the A2aR antagonist is a small molecule. In certain embodiments, the A2aR antagonist is CPI-444, PBF-509, istradefylline (KW-6002), preladenant (SCH420814), tozadenant (SYN115), vipadenant (BIIB014), HTL-1071, ST1535, SCH412348, SCH442416, SCH58261, ZM241385, or AZD4635.

In one embodiment, the immune checkpoint inhibitor is a CEACAM1 antagonist. In some embodiments, the CEACAM1 antagonist is an anti-CEACAM1 antibody or antigen binding fragment thereof. In one embodiment, the anti-CEACAM1 antibody is CM-24 (MK-6018).

In one embodiment, the immune checkpoint inhibitor is a CEA antagonist. In one embodiment, the CEA antagonist is an anti-CEA antibody or antigen binding fragment thereof. In certain embodiments, the anti-CEA antibody is cergutuzumab amunaleukin (RG7813, RO-6895882) or RG7802 (RO6958688).

In one embodiment, the immune checkpoint inhibitor is a CD47 antagonist. In some embodiments, the CD47 antagonist is an anti-CD47 antibody or antigen binding fragment thereof. In certain embodiments, the anti-CD47 antibody is HuF9-G4, CC-90002, TTI-621, ALX148, NI-1701, NI-1801, SRF231, or Effi-DEM.

In one embodiment, the immune checkpoint inhibitor is a PVRIG antagonist. In certain embodiments, the PVRIG antagonist is an anti-PVRIG antibody or antigen binding fragment thereof. In one embodiment, the anti-PVRIG antibody is COM701 (CGEN-15029).

In one embodiment, the immune checkpoint inhibitor is a TDO antagonist. In one embodiment, the TDO antagonist is a 4-(indol-3-yl)-pyrazole derivative, a 3-indol substituted derivative, or a 3-(indol-3-yl)-pyridine derivative. In another embodiment, the immune checkpoint inhibitor is a dual IDO and TDO antagonist. In one embodiment, the dual IDO and TDO antagonist is a small molecule.

In one embodiment, the immune checkpoint inhibitor is a VISTA antagonist. In some embodiments, the VISTA antagonist is CA-170 or JNJ-61610588.

In one embodiment, one or more of the drugs of the drug delivery device 12 is an immune checkpoint enhancer or stimulator.

In one embodiment, the immune checkpoint enhancer or stimulator is a CD28 agonist, a 4-1BB agonist, an OX40 agonist, a CD27 agonist, a CD80 agonist, a CD86 agonist, a CD40 agonist, an ICOS agonist, a CD70 agonist, or a GITR agonist.

In one embodiment, the immune checkpoint enhancer or stimulator is an OX40 agonist. In certain embodiments, the OX40 agonist is an anti-OX40 antibody or antigen binding fragment thereof. In some embodiments, the anti-OX40 antibody is tavolixizumab (MEDI-0562), pogalizumab (MOXR0916, RG7888), GSK3174998, ATOR-1015, MEDI-6383, MEDI-6469, BMS 986178, PF-04518600, or RG7888 (MOXR0916). In another embodiment, the OX40 agonist is a cell based therapy. In certain embodiments, the OX40 agonist is a GINAKIT cell (iC9-GD2-CD28-OX40-expressing T lymphocytes).

In one embodiment, the immune checkpoint enhancer or stimulator is a CD40 agonist. In some embodiments, the CD40 agonist is an anti-CD40 antibody or antigen binding fragment thereof. In one embodiment, the anti-CD40 antibody is ADC-1013 (JNJ-64457107), RG7876 (RO-7009789), HuCD40-M2, APX005M (EPI-0050), or Chi Lob 7/4. In another embodiment, the CD40 agonist is a soluble CD40 ligand (CD40-L). In one embodiment, the soluble CD40 ligand is a fusion polypeptide. In certain embodiments, the soluble CD40 ligand is a trimeric CD40-L (AVREND®).

In one embodiment, the immune checkpoint enhancer or stimulator is a GITR agonist. In certain embodiments, the GITR agonist is an anti-GITR antibody or antigen binding fragment thereof. In one embodiment, the anti-GITR antibody is BMS-986156, TRX518, GWN323, INCAGN01876, or MEDI1873. In one embodiment, the GITR agonist is a soluble GITR ligand (GITRL). In some embodiments, the soluble GITR ligand is a fusion polypeptide. In another embodiment, the GITR agonist is a cell based therapy. In one embodiment, the cell based therapy is an anti-CTLA4 mAb RNA/GITRL RNA-transfected autologous dendritic cell vaccine or a GITRL RNA-transfected autologous dendritic cell vaccine.

In one embodiment, the immune checkpoint enhancer or stimulator a 4-1BB agonist. In some embodiments, the 4-1BB agonist is an anti-4-1BB antibody or antigen binding fragment thereof. In one embodiment, the anti-4-1BB antibody is urelumab or PF-05082566.

In one embodiment, the immune checkpoint enhancer or stimulator is a CD80 agonist or a CD86 agonist. In some embodiments, the CD80 agonist or the CD86 agonist is a soluble CD80 or CD86 ligand (CTLA-4). In certain embodiments, the soluble CD80 or CD86 ligand is a fusion polypeptide. In one embodiment, the CD80 or CD86 ligand is CTLA4-Ig (CTLA4-IgG4m, RG2077, or RG1046) or abatacept (ORENCIA, BMS-188667). In other embodiments, the CD80 agonist or the CD86 agonist is a cell based therapy. In one embodiment, the cell based therapy is MGN1601 (an allogeneic renal cell carcinoma vaccine).

In one embodiment, the immune checkpoint enhancer or stimulator is a CD28 agonist. In some embodiments, the CD28 agonist is an anti-CD28 antibody or antigen binding fragment thereof. In certain embodiments, the anti-CD28 antibody is TGN1412.

In one embodiment, the CD28 agonist is a cell based therapy. In certain embodiments, the cell based therapy is JCAR015 (anti-CD19-CD28-zeta modified CAR CD3+T lymphocyte); CD28CAR/CD137CAR-expressing T lymphocyte; allogeneic CD4+ memory Th1-like T cells/microparticle-bound anti-CD3/anti-CD28; anti-CD19/CD28/CD3zeta CAR gammaretroviral vector-transduced autologous T lymphocytes KTE-C19; anti-CEA IgCD28TCR-transduced autologous T lymphocytes; anti-EGFRvIII CAR-transduced allogeneic T lymphocytes; autologous CD123CAR-CD28-CD3zeta-EGFRt-expressing T lymphocytes; autologous CD171-specific CAR-CD28 zeta-4-1-BB-EGFRt-expressing T lymphocytes; autologous CD19CAR-CD28-CD3zeta-EGFRt-expressing Tcm-enriched T cells; autologous PD-1-targeted chimeric switch receptor-modified T lymphocytes (chimera with CD28); CD19CAR-CD28-CD3zeta-EGFRt-expressing Tcm-enriched T lymphocytes; CD19CAR-CD28-CD3zeta-EGFRt-expressing Tn/mem-enriched T lymphocytes; CD19CAR-CD28zeta-4-1BB-expressing allogeneic T lymphocytes; CD19CAR-CD3zeta-4-1BB-CD28-expressing autologous T lymphocytes; CD28CAR/CD137CAR-expressing T lymphocytes; CD3/CD28 costimulated vaccine-primed autologous T lymphocytes; or iC9-GD2-CD28-OX40-expressing T lymphocytes.

In one embodiment, the immune checkpoint enhancer or stimulator is a CD27 agonist. In certain embodiments, the CD27 agonist is an anti-CD27 antibody or antigen binding fragment thereof. In one embodiment, the anti-CD27 antibody is varlilumab (CDX-1127).

In one embodiment, the immune checkpoint enhancer or stimulator is a CD70 agonist. In some embodiments, the CD70 agonist is an anti-CD70 antibody or antigen binding fragment thereof. In one embodiment, the anti-CD70 antibody is ARGX-110.

In one embodiment, the immune checkpoint enhancer or stimulator is an ICOS agonist. In certain embodiments, the ICOS agonist is an anti-ICOS antibody or antigen binding fragment thereof. In some embodiments, the anti-ICOS antibody is BMS986226, MEDI-570, GSK3359609, or JTX-2011. In other embodiments, the ICOS agonist is a soluble ICOS ligand. In some embodiments, the soluble ICOS ligand is a fusion polypeptide. In one embodiment, the soluble ICOS ligand is AMG 750.

In one embodiment, one or more of the drugs of the drug delivery device 12 is an anti-CD73 antibody or antigen binding fragment thereof. In certain embodiments, the anti-CD73 antibody is MEDI9447.

In one embodiment, one or more of the drugs of the drug delivery device 12 is a TLR9 agonist. In one embodiment, the TLR9 agonist is agatolimod sodium.

In one embodiment, one or more of the drugs of the drug delivery device 12 is a cytokine. In certain embodiments, the cytokine is a chemokine, an interferon, an interleukin, lymphokine, or a member of the tumor necrosis factor family. In some embodiments, the cytokine is IL-2, IL-15, or interferon-gamma.

In one embodiment, one or more of the drugs of the drug delivery device 12 is a TGF-β antagonist. In some embodiments, the TGF-β antagonist is fresolimumab (GC-1008); NIS793; IMC-TR1 (LY3022859); ISTH0036; trabedersen (AP 12009); recombinant transforming growth factor-beta-2; autologous HPV-16/18 E6/E7-specific TGF-beta-resistant T lymphocytes; or TGF-b eta-resistant LMP-specific cytotoxic T-lymphocytes.

In one embodiment, one or more of the drugs of the drug delivery device 12 is an iNOS antagonist. In some embodiments, the iNOS antagonist is N-Acetyle-cysteine (NAC), aminoguanidine, L-nitroarginine methyl ester, or S,S-1,4-phenylene-bis(1,2-ethanediyl)bis-isothiourea).

In one embodiment, one or more of the drugs of the drug delivery device 12 is a SHP-1 antagonist.

In one embodiment, one or more of the drugs of the drug delivery device 12 is a colony stimulating factor 1 receptor ("CSF1R") antagonist. In certain embodiments, the CSF1R antagonist is an anti-CSF1R antibody or antigen binding fragment thereof. In some embodiments, the anti-CSF1R antibody is emactuzumab.

In one embodiment, one or more of the drugs of the drug delivery device 12 is an agonist of a TNF family member. In some embodiments, the agonist of the TNF family member is ATOR 1016, ABBV-621, or Adalimumab.

In one embodiment, one or more of the drugs of the drug delivery device 12 is aldesleukin, bempegaldesleukin, tocilizumab, or MEDI5083. In one embodiment, the delivery device 12 includes bempegaldesleukin and a PD-1 pathway inhibitor, e.g., nivolumab (OPDIVO) or pembrolizumab (KEYTRUDA). In one embodiment, the delivery device 12 includes bempegaldesleukin and a LAG3 antagonist, e.g., relatlimab or MK-4280. In one embodiment, the delivery device 12 includes bempegaldesleukin, a PD-1 pathway inhibitor, e.g., nivolumab (OPDIVO) or pembrolizumab (KEYTRUDA), and a LAG3 antagonist, e.g., relatlimab or MK-4280. In one embodiment, the delivery device 12 includes bempegaldesleukin and a CTLA-4 antagonist, e.g., ipilimumab (YERVOY).

In one embodiment, one or more of the drugs of the drug delivery device 12 is a CD160 (NK1) agonist. In certain embodiments, the CD160 (NK1) agonist is an anti-CD160 antibody or antigen binding fragment thereof. In one embodiment, the anti-CD160 antibody is BY55.

What is claimed is:

1. A combinatorial drug delivery device for delivering a predetermined selection of drug components, each of the drug components being contained in a drug vial, the device comprising:
   a plurality of modules serially connected along a longitudinal axis, wherein each of the modules includes:
   a body having an interior volume formed to accommodate a drug vial;
   a cannula protruding into the interior volume, the cannula terminating at a free end, first and second openings being formed in the free end with first and second lumens extending therefrom and through the cannula;
   a socket located on a first side wall of the body;
   a first passageway extending between, and in communication with, the socket and the first lumen;
   a boss protruding from a second side wall of the body in a direction parallel to the longitudinal axis, the first and second side walls being on opposite sides of the body; and,
   a second passageway extending from, and in communication with the second lumen, the second passageway extending through the boss to terminate at an exit opening formed therein;
   a housing having a discharge passageway extending from a housing side wall, wherein a first module of the modules is coupled to the housing with i. the housing side wall facing the second side wall of the first module, and, ii. the second passageway of the first module being in communication with the discharge passageway, and, wherein a second module of the modules is coupled to the first module with i. the first side wall of the first module facing the second side wall of the second module, and. ii. the second passageway of the second module being in communication with the first passageway of the first module, the first module being located between the second module and the housing; and,
   a source of negative pressure for drawing the drug components from the drug vials of the modules and into the discharge passageway, wherein the source of negative pressure is located inside the housing.

2. A device as in claim 1, wherein each of the modules includes a vial retainer movably disposed on the body.

3. A device as in claim 2, wherein the vial retainer is hingedly mounted to the body.

4. A device as in claim 2, wherein the vial retainer is rotatably mounted to the body.

5. A device as in claim 2, wherein the vial retainer is translatable relative to the body.

6. A device as in claim 1, wherein each of the modules further comprising a venting passageway extending between, and in communication with, a vent opening formed on an exterior portion of the body and the first passageway.

7. A device as in claim 1, further comprising discharge tubing in communication with the discharge passageway.

8. A device as in claim 1, wherein the socket and the boss of adjacent coupled modules are configured to lock together.

9. A device as in claim 1, wherein the housing includes a controller for controlling the source of negative pressure.

10. A device as in claim 9, wherein the housing includes a power source for the source of negative pressure.

11. A device as in claim 1, wherein the source of negative pressure is a pump located inside of the housing, and wherein the housing includes a controller for controlling the pump.

12. A device as in claim 1, wherein, for each of the modules, the body is formed to wholly encase the accommodated drug vial.

* * * * *